United States Patent [19]

Huang et al.

[11] Patent Number: 5,292,981
[45] Date of Patent: Mar. 8, 1994

[54] ISOPARAFFIN-OLEFIN ALKYLATION PROCESS

[75] Inventors: Tracy J. Huang, Lawrenceville, N.J.; Reuel Shinnar, Great Neck, N.Y.

[73] Assignee: Mobil Oil Corporation, Fairfax, Va.

[21] Appl. No.: 899,537

[22] Filed: Jun. 16, 1992

[51] Int. Cl.$^5$ .............................................. C07C 2/62
[52] U.S. Cl. .................................. 585/722; 585/714; 585/716; 585/719; 585/720; 585/922; 585/924; 502/34; 502/41
[58] Field of Search ............... 585/714, 716, 717, 719, 585/720, 722; 502/34, 41

[56] References Cited

U.S. PATENT DOCUMENTS

| | | | |
|---|---|---|---|
| 3,917,738 | 11/1975 | Fenske et al. | 260/683.43 |
| 4,065,381 | 12/1977 | Say et al. | 208/134 |
| 4,384,161 | 5/1983 | Huang | 585/722 |
| 4,918,255 | 4/1990 | Chou et al. | 585/331 |
| 4,992,615 | 2/1991 | Huss, Jr. et al. | 585/722 |
| 5,095,167 | 3/1992 | Christensen | 585/720 |
| 5,157,196 | 10/1992 | Crossland et al. | 585/720 |

Primary Examiner—Asok Pal
Attorney, Agent, or Firm—Alexander J. McKillop; Dennis P. Santini; Laurence P. Hobbes

[57] ABSTRACT

A process for isoparaffin-olefin alkylation is provided that permits the use of solid acid catalysts which require frequent regeneration and high isoparaffin/olefin ratios. The process comprises circulating in a reactor a slurry comprising solid acid zeolite catalyst particles (20–2000 microns) and feed of liquid reactants comprising isoparaffins and olefins in an isoparaffin to olefin molar ratio of less than 100, recycling a first portion of said slurry to provide an isoparaffin to olefin molar ratio in the reactor of at least 500, passing a second portion of the slurry to a separating means to separate alkylate product from said solid catalyst particles, and regenerating the catalyst particles.

28 Claims, 2 Drawing Sheets

ISOPARAFFIN-OLEFIN ALKYLATION PROCESS

BACKGROUND OF THE INVENTION

The present invention relates to an isoparaffin-olefin alkylation process carried out in a circulating slurry reactor containing a slurry comprising fluidizable solid acid zeolite catalyst of particles whose largest dimension ranges from 20-2000 microns and liquid reactants and products, wherein a portion of said slurry is recycled at very high rates to provide a very high isoparaffin to olefin molar ratio, while a second portion of the slurry is passed to a separating means to separate reactants and products from the catalyst, regenerating the catalyst, optionally recycling the separate reactants to the reactor, and collecting the alkylate product which is useful, inter alia, as an octane enhancer for gasoline.

As a result of the curtailment in the use of tetraethyl lead as an octane-improving additive for gasoline, not only has the production of unleaded gasoline increased but the octane number specification of all grades of gasoline have increased as well. Isoparaffin-olefin alkylation is a key route to the production of highly branched paraffin octane enhancers which are to be blended into gasolines.

Alkylation involves the addition of an alkyl group to an organic molecule. Thus, an isoparaffin can be reacted with an olefin to provide an isoparaffin of higher molecular weight. Industrially, alkylation often involves the reaction of $C_2$–$C_5$ olefins with isobutane in the presence of an acidic catalyst. Alkylates are valuable blending components for the manufacture of premium gasolines due to their high octane ratings.

In the past, alkylation processes have included the use of hydrofluoric acid or sulfuric acid as catalysts under controlled temperature conditions. Low temperatures are utilized in the sulfuric acid process to minimize the undesirable side reaction of olefin polymerization and the acid strength is generally maintained at 88-94 percent by the continuous addition of fresh acid and the continuous withdrawal of spent acid. The hydrofluoric acid process is less temperature-sensitive and the acid is easily recovered and purified.

The typical types of alkylation currently used to produce high octane gasoline blending component, that is, the hydrofluoric acid and sulfuric acid alkylation processes, have inherent drawbacks including environmental concerns, acid consumption and disposal of corrosive materials. With the increasing demands for octane and the increasing environmental concerns, it has been desirable to develop an alkylation process based on a solid catalyst system. The catalyst of the present invention offers a refiner a more environmentally acceptable alkylation process than the currently used hydrofluoric and sulfuric acid alkylation processes.

Crystalline metallosilicates, or zeolites, have been widely investigated for use in the catalysis of isoparaffin alkylation. For example, U.S. Pat. No. 3,251,902 describes the use of a fixed bed of ion-exchanged crystalline aluminosilicate having a reduced number of available acid sites for the liquid phase alkylation of $C_4$–$C_{20}$ branched-chain paraffins with $C_2$–$C_{12}$ olefins in which the molar ratio of isoparaffin to olefin is generally greater than 3 to 1. The patent further discloses that the $C_4$–$C_{20}$ branched-chain paraffin should be allowed to substantially saturate the crystalline aluminosilicate before the olefin is introduced to the alkylation reactor.

U.S. Pat. No. 3,450,644 discloses a method for regenerating a zeolite catalyst used in hydrocarbon conversion processes involving carbonium ion intermediates.

U.S. Pat. No. 3,549,557 describes the alkylation of isobutane with $C_2$–$C_3$ olefins using certain crystalline aluminosilicate zeolite catalysts, e.g., rare earth-exchanged zeolite Y, in a fixed, moving or fluidized bed system, the olefin being preferably injected at various points in the reactor.

U.S. Pat. No. 3,644,565 discloses the alkylation of a paraffin with an olefin in the presence of a catalyst comprising a Group VIII noble metal present on a crystalline aluminosilicate zeolite, the catalyst having been pretreated with hydrogen to promote selectivity.

U.S. Pat. No. 3,647,916 describes an isoparaffin-olefin alkylation process featuring the use of an ion-exchanged crystalline aluminosilicate, isoparaffin/olefin mole ratios below 3:1 and regeneration of the catalyst.

U.S. Pat. No. 3,655,813 discloses a process for alkylating $C_4$–$C_5$ isoparaffins with $C_3$–$C_9$ olefins using a crystalline aluminosilicate zeolite catalyst wherein a halide adjuvant is employed in the alkylation reactor. The isoparaffin and olefin are introduced into the alkylation reactor at specified concentrations and catalyst is continuously regenerated outside the alkylation reactor.

U.S. Pat. No. 3,893,942 describes an isoparaffin alkylation process employing, as catalyst, a Group VIII metal-containing zeolite which is periodically hydrogenated with hydrogen in the gas phase to reactivate the catalyst when it has become partially deactivated.

U.S. Pat. No. 3,236,671 discloses the use, in alkylation, of crystalline aluminosilicate zeolites having silica to alumina mole ratios above 3 and also discloses the use of various metals exchanged and/or impregnated on such zeolites.

U.S. Pat. No. 3,706,814 discloses another zeolite-catalyzed isoparaffin-olefin alkylation process and further provides for the addition of $C_5+$ paraffins such as Udex raffinate or $C_5+$ olefins to the alkylation reactor feed and the use of specific reactant proportions, halide adjuvants, etc.

U.S. Pat. No. 3,624,173 discloses the use, in isoparaffin-olefin alkylation, of zeolite catalysts containing gadolinium.

U.S. Pat. No. 3,738,977 discloses alkylation of paraffins with ethylene employing a zeolite catalyst which possesses a Group VIII metal component, the catalyst having been pretreated with hydrogen.

U.S. Pat. No. 3,865,894 describes the alkylation of $C_4$–$C_6$ isoparaffin with $C_3$–$C_9$ monoolefin employing a substantially anhydrous acidic zeolite, for example acidic zeolite Y (zeolite HY), and a halide adjuvant.

U.S. Pat. No. 3,917,738 describes a process for alkylating an isoparaffin with an olefin using a solid, particulate catalyst capable of absorbing the olefin. The isoparaffin and the olefin are admixed to form a reactant stream in contact with catalyst particles at the upstream end of an adsorption zone after which the reactants are passed concurrently with the catalyst so that a controlled amount of olefin is adsorbed onto the catalyst before the combination of reactants and catalyst is introduced into an alkylation zone. This controlled olefin adsorption is said to prevent polymerization of the olefin during alkylation.

U.S. Pat. No. 4,377,721 describes an isoparaffin-olefin alkylation process utilizing, as catalyst, ZSM-20, preferably HZSM-20 or rare earth cation-exchanged ZSM-20.

U.S. Pat. No. 4,065,381 describes a process utilizing a draft tube for hydrogen stripping of HF from an extract containing metal pentafluoride and HF resulting from hydrocarbon conversions using Friedel-Crafts catalysts, e.g., alkylation.

U.S. Pat. No. 4,384,161 describes a process of alkylating isoparaffins with olefins to provide alkylate employing as catalyst a large pore zeolite capable of absorbing 2,2,4-trimethylpentane, e.g., ZSM-4, ZSM-20, ZSM-3, ZSM-18, zeolite Beta, faujasite, mordenite, zeolite Y and the rare earth metal-containing forms thereof, and a Lewis acid such as boron trifluoride, antimony pentafluoride or aluminum trichloride. The use of a large pore zeolite in combination with a Lewis acid in accordance with this patent is reported to greatly increase the activity and selectivity of the zeolite thereby effecting alkylation with high olefin space velocity and low isoparaffin/olefin ratio.

U.S. Pat. No. 5,095,167 describes a process and apparatus for alkylating isoparaffin with an olefin which decreases catalyst inventory required while improving alkylate quality by internally admixing unreacted isoparaffin and alkylate product with the reactant stream in the draft tube of a decantation reaction vessel.

U.S. Pat. No. 4,992,615 describes a process for alkylating isoparaffins with olefins to provide alkylate using MCM-22 catalyst.

U.S. Pat. No. 4,918,255 describes a process for alkylating isoparaffin with olefin to provide a product having a high proportion of highly branched paraffins using a composite catalyst comprising a Lewis acid with large pore zeolite in the presence of a controlled amount of water. Suitable large pore zeolites include ZSM-3, ZSM-4, ZSM-12, ZSM-18, ZSM-20, zeolite Beta, zeolite L, mordenite, faujasite and Zeolite Y.

All of the above disclosures are incorporated herein by reference.

Processes employing solid catalysts suffer from problems in that the catalysts tend to age rapidly and are unable to perform effectively at high olefin space velocities unless they are promoted with a Lewis acid such as boron trifluoride, $BF_3$, antimony pentafluoride, $SbF_5$, and aluminum chloride, $AlCl_3$. However, such promoted catalysts involve the use of corrosive and hazardous materials. Accordingly, although methods capable of using unpromoted solid acid catalysts would be desirable, such unpromoted catalysts are known to have a low selectivity for alkylation versus olefin polymerization and require frequent regeneration.

SUMMARY OF THE INVENTION

In accordance with the present invention, a process is provided for isoparaffin-olefin alkylation using solid acid catalysts which allows frequent regeneration of the catalyst and allows recycle of the catalyst after stripping. The process comprises circulating in a reactor a slurry comprising solid acid zeolite catalyst particles whose largest dimension ranges from 20 to 2000 microns and feed to the reactor of liquid reactants comprising isoparaffins and olefins in an isoparaffin to olefin molar ratio of less than 50. A first portion of the slurry is directly recycled and combined with the feed to provide an effective isoparaffin to olefin molar ratio in the reactor of at least 500. A second portion of the slurry is passed to a separating means to separate alkylate product from the solid catalyst particles which are passed to a regenerating means. Optionally, the clarified recycle, containing reactants is recycled by combining with the feed to the reactor. The method permits removal of a slip stream of catalyst for regeneration outside the isoparaffin/olefin alkylation reactor.

The process of the present invention is adapted to the use of non-Lewis acid-promoted acid solid zeolite catalyst in very fine particle form. Such catalysts require a very high local isoparaffin to olefin ratio. This is due to the fact that while the zeolite catalysts have a very high alkylation activity, the inherent selectivity to alkylation versus the undesirable polymerization is lower than in hydrofluoric acid. The only way to overcome this is to ensure that in the vicinity of a catalyst particle the local isoparaffin to olefin ratio is very high. In a small stirred tank this is quite easy to achieve but in larger reactors this is harder to achieve. The invention described in the following presents a unique design that guarantees a high minimum ratio of isobutane to olefin at any point the reactants contact the catalyst.

Another well known problem affecting such catalysts is that catalysts deactivate due to polymer formation and need to be regenerated. The active life span of a catalyst varies from several hours to several days. Continuous regeneration is, therefore, required; and the invention presents a unique continuous regeneration scheme suitable for a slurry reactor.

Isoparaffin-light olefin alkylation plays an important role in the manufacture of high octane gasoline blending stocks with alkylate typically comprising 10–15% of the gasoline pool. Alkylate is an especially valuable component of the gasoline pool as it possesses both high research and motor octane (low sensitivity) numbers, contains no olefins or aromatics and little or no sulfur, demonstrates excellent stability and is clean burning. One measure of the selectivity of an alkylation catalyst is the $C_9+$ yield. This fraction generally results from oligomerization of the feed olefins resulting in a loss of alkylate yield, reduced alkylate quality and the possible formation of an acidic sludge fraction. The alkylate produced by the process of this invention is of high quality based on both research and motor octane numbers and as such is particularly well suited for blending into the gasoline pool.

DESCRIPTION OF SPECIFIC EMBODIMENTS

Figure 1:
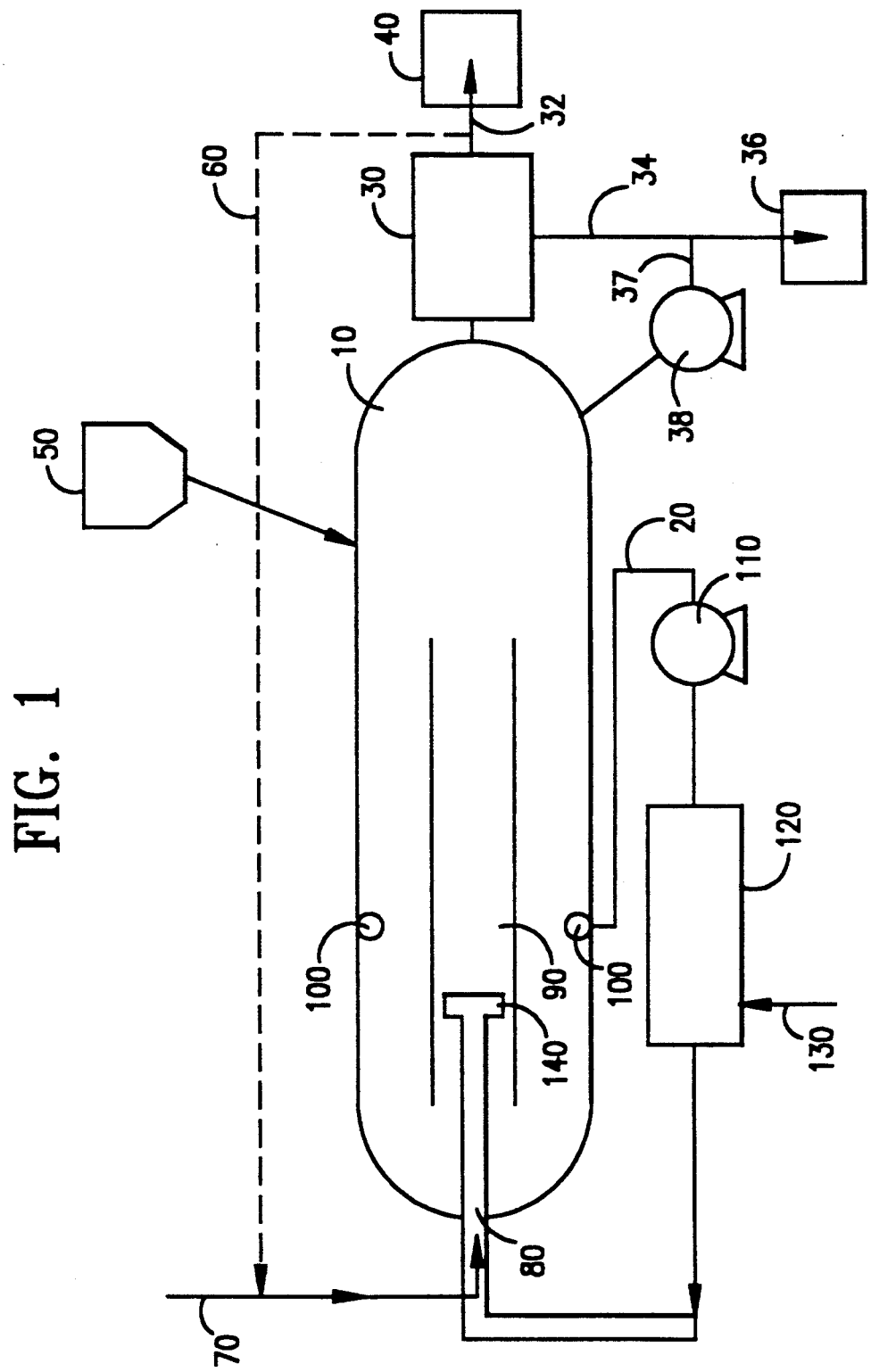
FIG. 1 depicts the circulating slurry reactor used in the production of alkylate.
Figure 2:
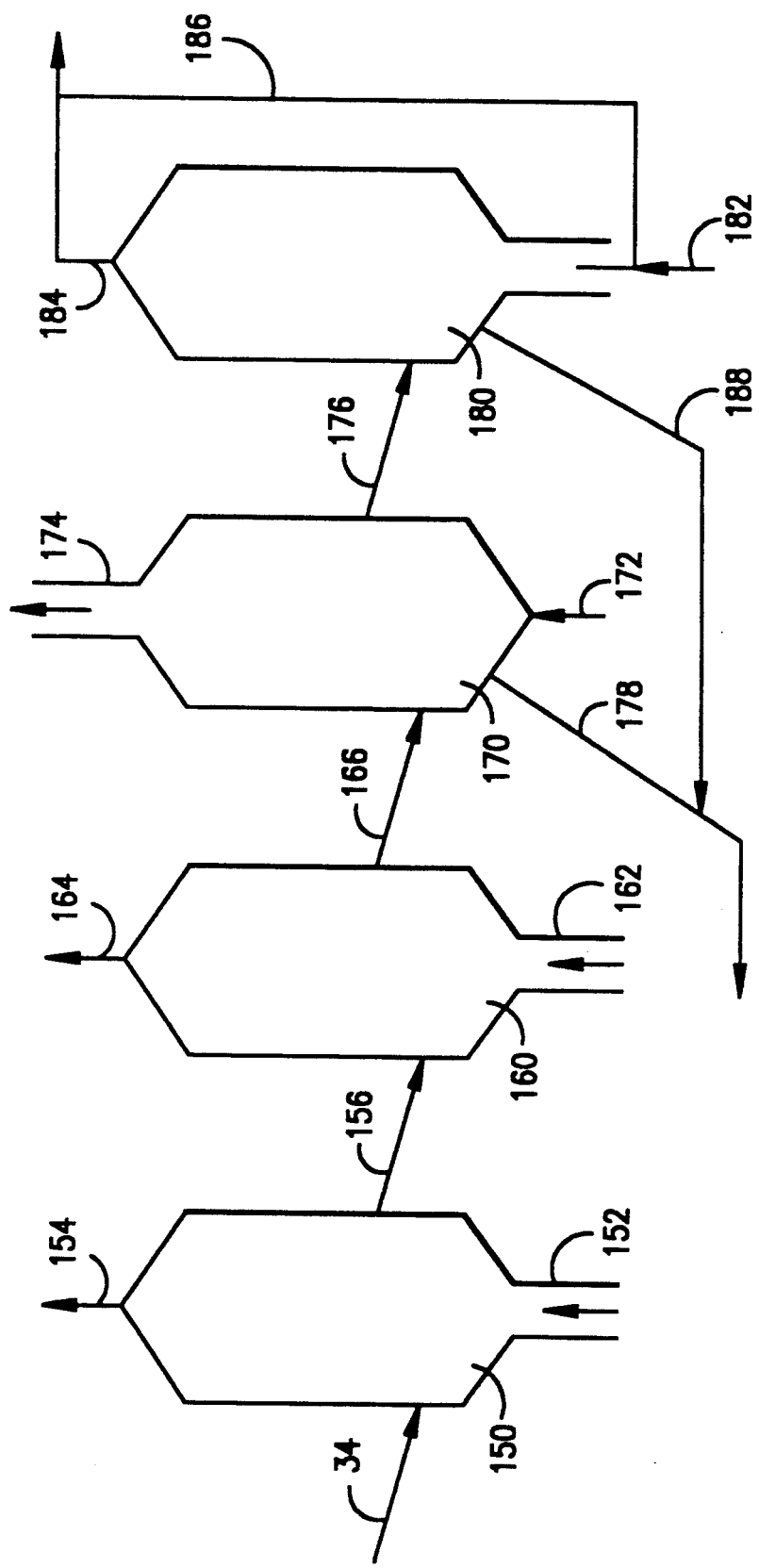
FIG. 2 depicts the regeneration scheme used in the treatment of the depleted catalyst in the present invention.

Having thus described the invention in general terms, reference is now made to FIGS. 1 and 2 which show an embodiment of the present invention. Such details are included as are necessary for a clear understanding of how the present invention may be employed. No intention is made to unduly limit the scope of the present invention to the particular configuration shown as variations are obvious to those having ordinary skill in the art of hydrocarbon conversion processes and are included within the broad scope of the present invention.

Referring now to FIG. 1, the present invention relates to a process for isoparaffin-olefin alkylation which comprises circulating in a reactor 10 a slurry comprising fluidizable solid acid zeolite catalyst particles whose largest diameter ranges from 20 to 2000 microns, preferably 50 to 200 microns, and feed of liquid reactants comprising isoparaffins and olefins in an isoparaffin to olefin molar ratio of less than 100, preferably between 10 and 50, typically about 15. The feed 70 is first diluted by a stream 60 containing the liquid contents of the slurry. This stream is obtained by taking a stream out of the reactor slurry and passing it together with the product stream through a set of hydrocyclones to remove the solid catalyst and then pumping it back to mix with the fresh feed. (Any solid liquid separation device could be substituted for the hydrocyclones.) As the isoparaffin to olefin ratio in the product stream is very high, this allows increasing the isobutane to olefin ratio in the total feed stream before it contacts the catalyst. In any conventional alkylation unit the feed stream is diluted by recycle isobutane before it is fed to the reactor. This recycle isobutane is obtained from the product stream by distillation. The same is done in our case as the fresh feed contains a high isobutane to olefin ratio. We have achieved an additional dilution by clarifying part of the reactor slurry and recycling the clarified slurry to the feed before it is fed to the reactor.

The dense catalyst slurry from unit 30 is partially fed back to the reactor via a pump and partially sent to the catalyst regeneration section (FIG. 2), discussed later.

A further dilution of the olefins or, in other words, a further increase of the isoparaffin to olefin ratio is obtained by rapid mixing of the total feed with the contents of the stirred reactor. If complete mixing could be achieved instantly, the isoparaffin to olefin ratio everywhere would be that of the product which is very high (preferably above 9,000). However, as the catalyst is very active, the mixing would have to be extremely fast which is hard to achieve in a large vessel. We here achieve this mixing in three stages. The first is by stream 60 mentioned above which is optional but preferable. The second is by a larger recycle stream 20 which consists of the reactor slurry. Stream 20 is passed through a heat exchanger in which the reaction heat is removed by either cooling water, or a cold brine in case the reactor is operated at a lower temperature. The velocity of stream 20 is high and it acts like an ejector pump to pump the reactor slurry through the draft tube to create a large mixing motion. Both the flow rate of the clarified slurry 60 and the recycle stream 20 can be adjusted to guarantee the required mixing rate in the reactor such as to avoid undesirable polymerization due to excess local olefin concentration.

This allows providing an isoparaffin to olefin molar ratio in the reactor of at least 500, preferably at least 1000, say at least 3000, or even at least 6000. A second portion of the slurry is passed to a separating means 30, e.g., a hydrocyclone, to, at least partially, separate alkylate product from the slurry which can be passed through line 32 to a means 40 for further isolating the alkylate product. The solid catalyst particles captured by the separating means 30 can be passed through line 34 to a regenerating means 36 or alternatively, recycled without regeneration through line 37 by means of a pump 38 to the reactor.

The reactor can be of any shape suited to alkylation, e.g., a large, long cylindrical vessel. Preferably the vessel is horizontally disposed to reduce pumping energy consumption although a vertical vessel can be used. The present method is particularly suited to high volume applications and reactor volume is preferably at least 50,000 gallons, and can be much larger, say, at least 100,000, 200,000 or 250,000 gallons.

The solid catalyst can be introduced to the reactor from a hopper 50 which is maintained under pressure, e.g., 100 to 5100 psig, preferably 150 to 1100 psig, say 200 to 700 psig, which may also contain isoparaffin, e.g., isobutane, as the pressurizing agent. Both new or regenerated catalyst can be introduced through the hopper. The solid catalyst is suspended in the liquid reactants and products in the reactor which is generally filled completely and maintained under liquid phase conditions. Such conditions comprise pressures within the reactor ranging from 0 to 5000 psig, preferably ranging from 50 to 1000 psig, say 100 to 600 psig. The resulting slurry is maintained at a solids content ranging from 2 to 40 vol %, preferably ranging from 6 to 30%.

In a preferred embodiment of the invention, the reactants are separated from the second portion of the slurry and recycled to the feed through line 60. This recycle stream is known as the clarified recycle. Because the clarified recycle generally has a much higher isoparaffin/olefin ratio than the feed, its mixing with the feed can further assist in providing a specified effective isoparaffin/olefin ratio, before the feed meets any catalyst. For example, clarified recycle having an isoparaffin/olefin ratio of say 500 to 10000, e.g, 3000, can be mixed with the feed having an isoparaffin/olefin ratio of, say 10 to 100, e.g, 15, which is passed through line 70. The feed in line 70 is mixed with the clarified recycle by use of an atomizing nozzle or any liquid mixing device. The recycle of the slurry in line 20 is generally not treated to remove solids and is known as the direct recycle. The direct recycle from line 20 can be introduced to the reactor separately from the feed but is preferably combined with the feed prior to introduction to the reactor through line 80.

Mixing in the reactor can be accomplished by any means suitable to effect homogeneous mixing of the catalyst/reactant-containing slurry so as to avoid the localized build-up of high olefin concentrations within the reactor. Although mechanical stirrers may be used, the present invention preferably utilizes a draft tube 90 which is open at both ends which is centrally disposed within the reactor. Highly effective mixing can be effected introducing the recycle of the slurry through the draft tube at high flow rates. The flow through the draft tube is preferably maintained at much higher levels than the direct recycle because the recycle is injected at a high velocity of at least 30 feet per second, preferably at 50 to 100 feet per second.

The direct recycle is preferably taken from that part of the reactor outside the draft tube. The intake to the direct recycle can be taken from ports 100 situated around the circumference of the reactor. The recycle is effected by means of a suitable impelling means, e.g., a pump 110, preferably a high capacity pump capable of pumping at least 10,000 gallons per minute of slurry, preferably at least 100,000 gallons per minute of slurry. The direct recycle can be passed through a heat exchanger 120 in order to remove the reaction heat generated in the reactor by the exothermic alkylation reaction heat from the flow of recycled slurry. The heat exchanger can utilize any suitable cooling medium, for example, water from line 130 maintained at 25° to 50° C., a fractionator bottom to utilize the heat if the reaction is carried out at 70° C., as a means for adjusting reactor temperature within optimal parameters. In cases where the operating temperature is below ambient temperature, a cooling system can be used.

After passing through the heat exchanger, the direct recycle is cycled back into the reactor through a line 80 which empties into the reactor, preferably within the draft tube, say in the upstream portion of the draft tube. The pipe can end in any suitable dispersion means, e.g., one or more atomizing nozzles 140, preferably a distributor coupled to a plurality of atomizing nozzles. The diluted feed is first admixed with this stream by atomizing it through nozzles or any other mixing device. It is important that the time elapsed between the addition of the prediluted fresh feed to the recycle stream and the mixing of the recycle stream with reactor contents flowing in the draft tube is very short. It is also important that the mixing intensity is high enough such that the feed is completely mixed with the clarified recycle before it contacts the slurry recycle. The direct recycle is varied in flow so as to achieve the desired minimum isoparaffin to olefin molar ratio. The total flow in the draft tube should reduce the olefin concentration to very low values, say, an isoparaffin to olefin molar ratio of at least 500, preferably at least 1000, or even at least 3000. To achieve such isoparaffin to olefin molar ratios, the slurry is recycled at a high rate with respect to the total reactor volume, e.g., a rate of at least 1 volume percent of total reactor volume per minute. Such rates can exceed 100 volume percent, or even 200 volume percent. Preferably, a slurry recycle rate of 5 to 60 volume percent of said total reactor volume per minute is used in the present invention.

In the reactor, the reactants are contacted with the acid solid catalyst particles under conditions which achieve their conversion to alkylates. Alkylate product can be collected by passing a second portion of the slurry in the reactor to separating means 30, e.g., a hydrocyclone, to separate alkylate product from the slurry. The remaining slurry from separating means 30 is further treated by passing it to the regenerator means 36 for further separating out the solid catalyst particles and combusting coke accumulated thereon. The regenerator means can be a series of fluid beds of decreasing pressure and increasing temperature from one bed to another, including the fluid bed regenerating means for the solid catalyst. In one embodiment, the series of fluid bed regenerators comprises a first fluid bed wherein the slurry from line 34 is heated to permit distilling off remaining liquid reactants and products, a second fluid bed wherein the resulting heated catalyst is steam stripped and a third fluid bed wherein the steam stripped catalyst is regenerated by combustion of the coked catalyst in the presence of air. The extent of combustion can be adjusted by diluting the oxygen source employed in the regeneration, e.g., air, with flue gas in order to reduce the oxygen content.

Another embodiment comprising four fluid beds is described by reference to FIG. 2. The first fluid bed 150 can be maintained at a pressure of 100 to 500 psig, preferably 200 to 300 psig, and a temperature of 100° to 250° C., preferably 120° to 200° C., and uses a suitable source of heat, e.g., steam, which is passed through line 152 to heat the slurry remaining in the hydrocyclone effluent (which is passed to the fluid bed through line 34) for further treatment by passing through line 154 to a condenser and product distillation column for distilling off remaining liquid reactants and products. The resulting heated catalyst is passed through line 156 to a second fluid bed 160 wherein the resulting heated catalyst is steam stripped by steam passing through line 162 and the stripped products passed through line 164 to a condenser, separator and distillation column. The second fluid bed can be maintained at a pressure of 25 to 100 psig, preferably 30 to 60 psig, and a temperature of 200° to 350° C., preferably 240° to 300° C. The remaining solid catalyst can be passed through line 166 to a subsequent fluid bed 170 maintained at a lower pressure, 25 to 50 psig, preferably 30 to 40 psig, and a higher temperature of 300° to 400° C., preferably 320° to 350° C., which further treats the solid catalyst with steam passed through line 172. Products and reactants coming off the solid catalyst are passed through line 174 to a condensor and separator. The solid catalyst remaining in the fluid bed at this stage can be recycled to the catalyst hopper through line 178 and/or transferred through line 176 to a fluid bed regenerator 180 which can be maintained at a pressure of 20 to 30 psig, say, 25 psig, and a temperature of 450° to 550° C., preferably 470° to 500° C., using a suitable source of oxygen passing through line 182, e.g., air, to effect regeneration by combustion of remaining organic materials on the catalyst. Flue gas is vented off through line 184 and/or recycled through line 186 to the fluid bed regenerator. The regenerated catalyst can be transferred by line 188 to the catalyst hopper for eventual recycle to the reactor.

The zeolites used in the present invention include those which have pores sufficiently large to physically absorb 2,2,4-trimethylpentane such as, for example, ZSM-3, ZSM-4, ZSM-12, ZSM-18, ZSM-20, zeolite Beta, zeolite L, mordenite, faujasite, zeolite X, zeolite Y, and MCM-22, and the rare earth metal containing forms of the above. A wide range of silica-to-alumina ratios, e.g., from at least about 2:1 to about 1000:1 can be used. For the purposes of this invention, zeolite Y includes zeolite Y in its as-synthesized form, as well as its variant forms including framework dealuminated zeolite Y, e.g., ultrastable Y (USY) described in U.S. Pat. No. 3,293,192 and LZ-210 described in U.S. Pat. No. 4,503,023. MCM-22 is further described in U.S. Pat. No. 4,992,615, incorporated herein by reference.

Prior to its use as alkylation catalyst herein, the zeolite crystals should be subjected to thermal treatment to remove part or all of any organic constituent present therein.

The zeolite alkylation catalyst herein can also be used in intimate combination with a hydrogenating component such as tungsten, vanadium, molybdenum, rhenium, nickel, cobalt, chromium, manganese, or a noble metal such as platinum or palladium. Such component can be associated chemically and/or physically with the zeolite and/or matrix with which the zeolite may be optionally composited. Thus, e.g., the hydrogenating component can be introduced into the catalyst composition by way of co-crystallization, exchanged into the composition to the extent a Group IIIA element, e.g., aluminum, is in the structure, impregnated therein or intimately physically admixed therewith. Such component can be impregnated in, or on, the zeolite such as, for example, by, in the case of platinum, treating the zeolite with a solution containing the platinum metal-containing ion. Thus, suitable platinum compounds for this purpose include chloroplatinic acid, platinous chloride and various compounds containing the platinum amine complex.

The zeolite, especially in its metal, hydrogen and ammonium forms, can be beneficially converted to another form by thermal treatment. This thermal treatment is generally performed by heating one of these forms at a temperature of at least about 370° C. for at least 1 minute and generally not longer than 20 hours. While subatmospheric pressure can be employed for the thermal treatment, atmospheric pressure is preferred simply for reasons of convenience. The thermal treatment can be performed at a temperature of up to about 925° C.

Prior to its use as alkylation catalyst in the process of this invention, the zeolite crystals should be at least partially dehydrated. This can be accomplished by heating the crystals to a temperature in the range of from about 200° C. to about 595° C. in an atmosphere such as air, nitrogen, etc., and at atmospheric, subatmospheric or superatmospheric pressures for a period of from between about 30 minutes to about 48 hours. Dehydration can also be performed at room temperature merely by placing the crystalline material in a vacuum but a longer time will be required to achieve a suitable degree of dehydration.

It may be desired to incorporate the zeolite crystalline material with another material, i.e., a binder, which is resistant to the temperatures and other conditions employed in the isoparaffin alkylation process of this invention. Suitable binder materials include active and inactive materials and synthetic or naturally occurring zeolites as well as inorganic materials such as clays, silica and/or metal oxides such as alumina. The latter can be either naturally occurring or provided in the form of gelatinous precipitates or gels including mixtures of silica and metal oxides. Use of a binder material in conjunction with the zeolite, i.e., combined therewith or present during its synthesis, which itself is catalytically active may change the conversion and/or selectivity of the catalyst. Inactive materials suitably serve as diluents to control the amount of conversion so that isoparaffin alkylation products can be obtained economically and in a controlled fashion without having to employ other means for controlling the rate of reaction. These materials can be incorporated into naturally occurring clays, e.g., bentonite and kaolin, to improve the crush strength of the zeolite under commercial isoparaffin alkylation operating conditions. Good crush strength is an advantageous attribute for commercial use since it prevents or delays breaking down of the catalyst into powder-like materials.

Naturally occurring clays which can be composited with zeolite crystals include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with zeolite also include inorganic oxides, notably alumina.

Apart from or in addition to the foregoing binder materials, the zeolite crystals can be composited with an inorganic oxide matrix such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia, silica-magnesia-zirconia, etc.

The relative proportions of finely divided crystalline material and inorganic oxide matrix can vary widely with the zeolite content ranging from about 1 to about 95 percent by weight and more usually, particularly when the composite is prepared in the form of beads, in the range of about 2 to about 80 weight percent of the composite.

The stability of the zeolite may be increased by combining the as-synthesized zeolite with an alumina binder, converting the alumina-bound zeolite to the hydrogen form, and steaming the alumina-bound, hydrogen-exchanged zeolite composition under conditions sufficient to increase the stability of the catalyst. U.S. Pat. Nos. 4,663,492; 4,594,146; 4,522,929; and, 4,429,176, the entire disclosures of which are incorporated herein by reference, describe conditions for the steam stabilization of zeolite catalysts which can be utilized to steam-stabilize alumina-bound zeolite. The steam stabilization conditions include contacting the alumina bound zeolite with, e.g., 5-100% steam at a temperature of at least about 300° C. (e.g., 300°-650° C.) for at least one hour (e.g., 1-200 hours) at a pressure of 101-2,500 kPa. In a more particular embodiment, the catalyst can be made to undergo steaming with 75-100% steam at 315°-500° C. and atmospheric pressure for 2-25 hours. In accordance with the steam stabilization treatment described in the above-mentioned patents, the steaming of the catalyst can take place under conditions sufficient to initially increase the Alpha Value of the catalyst, the significance of which is discussed infra, and produce a steamed catalyst having a peak Alpha Value. If desired, steaming can be continued to subsequently reduce the Alpha Value from the peak Alpha Value to an Alpha Value which is substantially the same as the Alpha Value of the unsteamed catalyst.

When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of a highly active silica-alumina cracking catalyst taken as an Alpha of 1 (Rate Constant=0.016 sec$^{-1}$). The Alpha Test which was used herein is described in *J. Catalysis*, 61, pp. 390-396 (1980), the contents of which are incorporated by reference herein. It is noted that intrinsic rate constants for many acid-catalyzed reactions are proportional to the Alpha Value for a particular crystalline silicate catalyst, i.e., the rates for toluene disproportionation, xylene isomerization, alkene conversion and methanol conversion (see "The Active Side of Acidic Aluminosilicate Catalysts," *Nature*, Vol. 309, No. 5969, pp. 589-591, 14 June 1984).

The operating temperature of the alkylation process herein can extend over a fairly broad range, e.g., from about −25° to about 200° C., and is preferably within the range of from about 40° C. to about 150° C. The practical upper operating temperature will often be dictated by the need to avoid an undue occurrence of undesirable side reactions.

The pressures employed in the present process can extend over a considerably wide range, e.g., from atmospheric pressure to about 5000 psig, and preferably from 150 psig to about 1000 psig.

The amount of zeolite used in the present alkylation process can be varied over relatively wide limits. In general, the amount of zeolite as measured by the weight hourly space velocity (WHSV) based on olefin can range from about 0.01 to about 100, preferably from 0.05 to 10. it will, of course, be realized by those skilled in the art that the amount of catalyst selected for a particular reaction will be determined by several variables including the reactants involved as well as the nature of the catalyst and the operating conditions employed.

The isoparaffin reactant used in the present alkylation process is one possessing up to about 20 carbon atoms and preferably one having from about 4 to about 8 carbon atoms as, for example, isobutane, 3-methylhexane, 2-methylbutane, 2,3-dimethylbutane and 2,4-dimethylhexane.

The olefin reactant employed herein generally contains from 2 to about 12 carbon atoms. Representative examples are ethylene, propylene, butene-1, butene-2, isobutylene, pentenes, hexanes, heptenes and octenes. Particularly preferred are $C_3$ and $C_4$ olefins and mixtures thereof.

The isoparaffin and/or olefin reactants can be in either the vapor phase or the liquid phase and can be neat, i.e., free from intentional admixture of dilution with other material, or the reactants can be brought into contact with the catalyst composition with the aid of carrier gases or diluents such as, for example, hydrogen or nitrogen.

The reactants can be introduced to the alkylation reaction zone together with one or more other materials which serve to enhance the overall conversion operation. Thus, for example, relatively small quantities of hydrogen and/or hydrogen donors can be present in the reaction zone to suppress catalyst aging. Water and/or materials such as alcohols which provide water under the alkylation conditions selected can also be introduced into the reaction zone for this purpose. Oxygen and/or other materials which tend to suppress oligomerization of the olefin feed can be present in the typically very small amounts which are effective to achieve this benefit. The optimum amounts of these optional materials which can be utilized to advantage in a particular alkylation operation can be readily determined by those skilled in the art employing routine experimentation.

The alkylation process of the present invention can be carried out as a continuous operation utilizing a circulating slurry comprising reactants and zeolite catalyst component. A slipstream of the slurry containing solid catalyst particles, is conducted to a separating means, e.g., a hydrocyclone to separate solid catalysts which are thereafter passed to a regeneration zone where coke is removed from the catalyst, e.g., by burning in an oxygen-containing atmosphere (such as air) at elevated temperature, after which the regenerated catalyst is recycled to the conversion zone for further contact with the organic reactants.

What is claimed is:

1. A process for isoparaffin-olefin alkylation which comprises the steps of:
    (a) introducing into a reactor fluidizable solid acid zeolite catalyst particles whose largest dimension ranges from 20–2000 microns;
    (b) introducing into the reactor a feed of liquid reactants comprising isoparaffins and olefins at a first isoparaffin to olefin molar ratio of less than 100;
    (c) forming a slurry of said catalyst particles and said feed and circulating said slurry within the reactor such that the isoparaffin reacts with the olefin to produce alkylate product and the isoparaffin to olefin molar ratio of the slurry increases to a value in excess of said first ratio;
    (d) removing a first portion of said slurry which comprises said alkylate product, olefin and isoparaffin, from the reactor and directly recycling said first portion at a rate of at least 5 volume percent of said total reactor volume per minute to mix with the feed and provide an isoparaffin to olefin molar ratio in the reactor of at least 500;
    (e) removing a second portion of the slurry from the reactor and passing said second portion to a separating means to separate alkylate product from the solid catalyst particles; and
    (f) regenerating the separated catalyst particles and recycling the regenerated catalyst particles to the reactor.

2. The process of claim 1 wherein said reactants are separated from said second portion of the slurry and recycled to the feed.

3. The process of claim 1 wherein said reactor comprises a draft tube open at both ends and wherein said first portion of said slurry is taken from outside of said draft tube.

4. The process of claim 3 wherein said feed is conveyed into said reactor through atomizing nozzles disposed within said draft tube.

5. The process of claim 1 wherein said slurry has a solids content ranging from 2 to 40 volume percent, said catalyst particles largest dimension ranges from 50 to 200 microns, said recycling of first portion of said slurry provides an isoparaffin to olefin molar ratio in the reactor of at least 1000, and said recycle is injected into the reactor at a velocity of at least 50 feet per second.

6. The process of claim 1 wherein said slurry has a solids content ranging from 6 to 30 volume percent, said recycling of first portion of said slurry provides an isoparaffin to olefin molar ratio in the reactor of at least 3000, and said recycle is injected into the reactor at a velocity of at least 100 feet per second.

7. The process of claim 1 wherein said reactor volume is greater than 50,000 gallons.

8. The process of claim 1 wherein said reactor volume is greater than 200,000 gallons.

9. The process of claim 1, wherein the reaction is carried out under sufficient pressure to maintain at least one of the reactants in the liquid phase.

10. The process of claim 1 wherein said slurry is recycled at a rate of 5 to 40 volume percent of said total reactor volume per minute.

11. The process of claim 3 wherein both said feed and said recycle are conveyed into said reactor through atomizing nozzles disposed within said draft tube.

12. The process of claim 1 wherein said reactor comprises a mechanical mixing means.

13. The process of claim 1 wherein said separating means comprises a hydrocyclone.

14. The process of claim 1 wherein said separated slurry catalyst particles are passed to a fluid bed regenerator.

15. The process of claim 14 wherein said separated catalyst particles are passed to a series of fluid beds of decreasing pressure and increasing temperature.

16. The process of claim 15 wherein said series of fluid bed regenerators comprises a first fluid bed wherein said resulting slurry is heated to permit distilling off remaining liquid reactants and products, a second fluidized bed wherein the resulting heated catalyst is steam stripped and a third fluid bed wherein said steam stripped catalyst is regenerated in the presence of air.

17. The process of claim 16 wherein said air is diluted with flue gas to reduce oxygen concentration.

18. The process of claim 16 wherein said regenerated catalyst is recycled to the reactor.

19. The process of claim 1 wherein said zeolite is rare earth-exchanged zeolite Y.

20. The process of claim 1, wherein the alkylation reaction temperature is from about −25° C. to about 200° C., the pressure is from atmospheric to about 5000 psig and the weight hourly space velocity based on olefin is from about 0.01 to 100.

21. The process of claim 1 wherein the zeolite is selected from the group consisting of faujasite, zeolite Y, ZSM-4, ZSM-20, and MCM-22.

22. The process of claim 1 wherein the zeolite has been treated to replace original cations, at least in part, with a cation or mixture of cations selected from the group consisting of hydrogen, hydrogen precursors, rare earth metals, and metals of Groups IIA, IIIA, IVA, IB, IIB, IIIB, IVB, VIB and VIII of the Periodic Table.

23. The process of claim 1, wherein the zeolite has been thermally treated at a temperature up to about 1700° F. in the presence or absence of steam.

24. The process of claim 13, wherein the zeolite has been thermally treated at a temperature up to about 1700° F. in the presence or absence of steam.

25. The process of claim 1 wherein the zeolite is combined with a binder.

26. The process of claim 16, wherein the binder is a silica-containing or an alumina-containing material.

27. The process of claim 1, wherein the isoparaffin contains from 4 to about 8 carbon atoms and the olefin contains from 2 to 12 carbon atoms.

28. The process of claim 1, wherein the isoparaffin is isobutane and the olefin is propylene and/or butene(s).

* * * * *